United States Patent [19]

Lumbert

[11] Patent Number: 4,981,466

[45] Date of Patent: * Jan. 1, 1991

[54] MEDICAL VENTILATING AND ASPIRATING APPARATUS AND METHODS

[76] Inventor: Richard C. Lumbert, 11225 No. 1 15 W. Frontage Rd., R.D. 1 Box 323D, Lehi, Utah 84043

[*] Notice: The portion of the term of this patent subsequent to May 30, 2006 has been disclaimed.

[21] Appl. No.: 265,637

[22] Filed: Nov. 1, 1988

Related U.S. Application Data

[63] Continuation of Ser. No. 24,429, Mar. 11, 1987, Pat. No. 4,834,776.

[51] Int. Cl.[5] ............................................. A61M 25/00
[52] U.S. Cl. ....................................... 604/19; 604/281
[58] Field of Search ........................... 604/19,280–282, 604/73, 21, 164, 165, 170; 128/305.3

[56] References Cited

U.S. PATENT DOCUMENTS

| | | | |
|---|---|---|---|
| 3,070,132 | 12/1962 | Sheridan | 604/280 |
| 3,363,629 | 1/1968 | Kuhn | 604/281 |
| 3,485,234 | 12/1969 | Stevens | 604/281 |
| 3,508,554 | 4/1970 | Sheridan | 604/280 |
| 3,605,750 | 9/1971 | Sheridan et al. | 604/280 |
| 3,612,038 | 10/1971 | Halligan | 604/281 |
| 3,633,758 | 1/1972 | Moise | 604/281 |
| 3,719,737 | 3/1973 | Vaillancourt | 604/281 |
| 3,935,857 | 2/1976 | Co | 604/281 |
| 3,991,762 | 11/1976 | Radford | 128/276 |
| 4,027,659 | 6/1977 | Slingluff | 604/280 |
| 4,050,667 | 9/1977 | Kossett | 604/281 |
| 4,275,724 | 6/1981 | Behrstock | 604/281 |
| 4,469,483 | 9/1984 | Becker et al. | 128/DIG. 21 |
| 4,569,344 | 2/1986 | Palmer | 128/207.16 |
| 4,632,112 | 12/1986 | Matthews | 128/305.3 |
| 4,638,539 | 1/1987 | Palmer | 29/157 |

OTHER PUBLICATIONS

Disposable Suction Catheter, *Nursing*, May 1979.
Suctioning the Left Bronchial Tree in the Intubated Adult, *Critical Care Medicine*, Freedman et al., vol. 10, No. 1, 1982.
Evaluation of Selective Bronchial Suctioning in the Adult, *Critical Care Medicine*, vol. 8, No. 12, 1980.
A New Controllable Suction Catheter for Blind Cannulation of the Main Stem Bronchi, *Critical Care Medicine*, vol. 6, No. 5, Sept.–Oct. 1978.
Evaluation of Selective Bronchial Suctioning Techniques Used for Infants and Children, *Anesthesiology*, 48:379–380.
Selective Bronchial Suctioning in the Adult Using a Curved–tipped Catheter with a Guide Mark, *Critical Care Medicine*, vol. 10, No. 11, Nov. 1982.
Selective Trachiobronchial Aspiration, *Thorax*, 32, 346–348, 1977.
Device for Determining Location of an Endotracheal Catheter Tip, *Critical Care Medicine*, vol. 12, No. 2, Feb. 1984.
Design and Function of Tracheal Suction Catheters, 1982.
The New NL Tracheal Suction Catheter, *Anesthesiology*, 1982.
Comparison of Trachiobronchial Suction Catheters in Humans, *Chest*, vol. 69, pp. 179–181, Feb. 1976.
Side Eye Position—Davol.
The Bear NVM-1 Neonatal Volume Monitor—Bear Medical Systems, Inc.

*Primary Examiner*—C. Fred Rosenbaum
*Assistant Examiner*—Kathleen A. Daley

[57] ABSTRACT

A ventilating/aspirating apparatus, and related methods, the apparatus comprising a catheter tube for evacuation of lung secretions wherein th distal end portion of the catheter tube is disposed at a substantial angle in respect to the remainder of the catheter tube whereby entry into the left lung of a patient may be predictably and accurately tended to without appreciable trauma to the patient. A removable angle retainer is provided for maintaining the configuration of the distal and portion of the catheter tube during storage, prior to use. Radiopaque indicia, selectively located within the wall of the catheter tube, is provided by which the entry of the distal end portion of the catheter tube into the lungs and particulary the left lung of the medical patient can be insured through accurate mointoring visually or by using available radiological techniques.

4 Claims, 1 Drawing Sheet

MEDICAL VENTILATING AND ASPIRATING APPARATUS AND METHODS

This application is a continuation of our copending U.S. patent application Ser. No. 24,429, filed Mar. 11, 1987, now U.S. Pat. No. 4,834,726.

FIELD OF INVENTION

The present invention relates generally to ventilation and aspiration of the lungs of a medical patient and, more particularly, to a novel ventilating and aspirating apparatus, and related methods, by which a suction catheter tube thereof can be predictably and accurately placed in either lung of a medical patient for removal of tracheobronchial secretions.

PRIOR ART

The most relevant, known aspirating/ventilating prior art patents are U.S. Pat. Nos. 3,991,762 and 4,569,344. In each case, an essentially linear catheter tube is provided for insertion into and removal of secretions from the lungs of a medical patient. Difficulty has been encountered in placing the catheter tube in the left lung of the patient and in verifying such placement. Often the technique required by the prior art is long term and traumatic for the patient. Clearing of secretions from the left lung sometimes does not occur, notwithstanding the belief of the physician, nurse or technician to the contrary.

The literature also confirms that the left lung is more difficult to enter with a suction catheter tube because of its greater angle of entry. The literature discloses curved-tip and angled-tip suction catheters, use of guide marks, in the form of dots, together with radiopaque liquid for catheter tip placement control of the length of the catheter to prevent kinking and avoidance of catheter rotation during placement.

BRIEF SUMMARY AND OBJECTS OF THE PRESENT INVENTION

In brief summary, the present invention is intended to overcome or substantially alleviate the aforementioned limitations of the prior art and comprises a novel ventilating/aspirating apparatus, and related methods, the apparatus comprising a catheter tube, for evacuation of lung secretions, having the non-linear distal end portion to facilitate ease and predictability of entry to either lung of a medical patient. In its presently preferred configuration, the distal end portion is disposed at a substantial angle in respect to the remainder of the catheter tube. An angle retainer is provided to maintain the angle during storage, prior to use. A unique method is provided for creating the angle in the wall of the catheter tube. Radiopaque indicia matching the configuration of the catheter tube is provided for the catheter tube by which the entry of the distal end portion of the catheter tube into the lungs, particularly the left lung, of the patient can be reasonably insured when blind placement is undertaken and absolutely assured through accurate monitoring, using existing radiological techniques.

Accordingly, it is a primary object of the present invention to provide a novel ventilating and aspirating apparatus, and related methods.

An important object of this invention is the provision of an aspirating/ventilating apparatus comprising a novel catheter tube for facile entry into either lung of a medical patient.

A further significant object of the present invention is the provision of an aspirating/ventilating apparatus comprising a novel secretion removing catheter tube having an angular distal end portion for easy and predictable entry into the left lung of a medical patient.

A further paramount object of the present invention is the provision of an aspirating/ventilating apparatus comprising a catheter tube having an angular distal end portion and a retainer for maintaining the shape of the distal end portion during storage prior to use.

A further valuable object of the present invention is the provision of an aspirating/ventilating apparatus comprising a novel secretion removing catheter tube having radiopaque indicia which matches the shape of the catheter tube and by which entry of the distal end of the catheter tube into a selected lung of a medical patient can be insured visually and/or through radiological monitoring.

It is another dominant object to provide a novel method for creating an angled-tip in a suction catheter tube.

These and other objects and features of the present invention will be apparent from the detailed description taken with reference to the accompanying drawings

DETAILED DESCRIPTION OF THE ILLUSTRATED EMBODIMENTS

Figure 4:
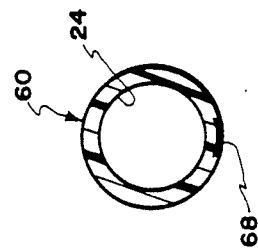
FIG. 4 is a cross-section taken along lines 4—4 of FIG. 3.

Removing secretions from the tracheobronchial tree is an integral part of the cre given to patients who are intubated and receiving mechanical or other artificial ventilation. Secretions can be excessive in some respiratory disorders and constitute a serious threat to the persons having such respiratory disorders. The presence of an endotracheal tube is a hindrance to the patient's efforts to clear secretions through natural coughing. Suction catheters are used to clear such secretions from the patient's airway.

The aspirating/ventilating apparatus disclosed in U.S. Pat. No. 4,569,344 is a device, which among other things, is used to clear secretions from the lungs of a patient. This device is attached to the patient's endotracheal tube and is included as part of an overall ventilation circuit. The suction catheter is enclosed within a plastic bag to eliminate or minimize contamination thereof. As the patient requires artificial removal of secretions, the suction catheter is advanced through a fitting of the ventilating device into the patient's airway and thence into a lung of the patient. Suction is thereafter applied to remove the secretions. The other lung may likewise be aspirated. The catheter is subsequently withdrawn into the plastic bag. Secretions are thus drawn into the lumen of the catheter tube and removed. The present invention is directed toward such suction catheter tubes normally forming part of a ventilating/aspirating apparatus of the type disclosed in U.S. Pat. No. 4,569,344.

The present invention is intended for accurate placement of an angled-tip suction catheter tube in either lung of a medical patient.

Reference is now made to the drawings wherein like numerals are used to designate like parts throughout. A presently preferred integrated ventilator/aspirating mechanism, generally designated 20, is illustrated in the drawings and embodies the principles of the present invention.

Ventilating/aspirating mechanism 20 is illustrated as being connected to a medical patient at a tracheostomy connector 26 or to an endotracheal tube which is left indwelling for repeated use over a protracted interval of time. Mechanism 20 comprises a central portion comprising a sterile internal aspirating catheter tube 22 having a hollow interior passageway 24 (FIG. 4) of sufficient capacity to aspirate secretions from the trachea and bronchus. The aspirating catheter tube 22 is formed of a suitable synthetic resinous material which is yieldable but shape-retaining when in an unstressed condition, such as medical grade transparent or translucent polyvinyl chloride and further comprises an annular wall essentially of uniform thickness throughout having typically small uniform inside and outside diameters. The outside diameter is selected to comfortably pass through the endotracheal tube, and into either lung of the patient.

The aspirating catheter tube 22 has sufficient strength to prevent buckling, bending and twisting of the catheter tube, which would otherwise occlude or tend to occlude the interior passageway of the catheter tube. In the assembled condition, the tube 22 is surrounded in sealed relation by a sterile sack or flexible envelope 28, formed of suitable impervious synthetic resinous film material of medical grade, such as polyethylene film in sleeve form.

The flexible envelope 28 is selectively attachable and detachable at each end, as explained herein, allowing ready manual manipulation of the catheter tube 22 by gripping action on the part of the user applied to the exterior of the envelope 28. The catheter tube 22 is controlled solely by manual manipulation thereof through the envelope.

The flexible envelope 28 is held by an interference fit at the opposite ends thereof by collars 30 and 32, respectively. The interference fit couplings 30 and 32 together with an aspirating vacuum controlled valve 40 and the tracheostomy tube connector 26 are illustrated as being of known components. These components are described in substantial detail in U.S. Pat. No. 4,569,344, the contents of which are incorporated herein by reference for purposes of simplifying this detailed description. It should be noted, however, that catheter tube 22 is in fluid communication with the valve 40, which in turn is in fluid communication with a vacuum source 42, such as a conventional hospital suction system. In short, when the catheter tube 22 is in the appropriate indwelling position in the lung of a medical patient, the valve 40 is manually actuated so that the vacuum of source 42 is applied to the hollow interior 24 of the catheter tube 22 thereby causing undesired secretions from the lung to enter the catheter tube through the tip openings 43 and to be removed via the hollow 24 of the catheter tube 22. The openings 43 and the open end of the catheter tube tip, at 24, are located to prevent plugging.

The connector 26 is illustrated as being in the form of a cross fitting. The fitting 26 provides an external seal against a loss of air or liquid pressures applied to a lung of a patient but accommodates snug slidable displacement of the catheter tube 22 through the fitting 26. The fitting 26 comprises first, second, third and fourth port structure 44, 46, 48 and 50. Ports 48 and 50 are illustrated as being closed by removable caps 51. Port structure 44 releasably connects through a fitting 52 to the distal end of the plastic envelope 28. Port structure 46 is appropriately fitted upon an exposed end of an endotracheal tube in the throat of the patient, while port structure 48 and 50, respectively, with the caps 51 remOved, connect to the output and exhaust terminals of a conventional ventilator 54. Thus, the ventilator 54 drives air through either port 48 or 50, respectively, with the caps 51 removed, connect to the output and exhaust terminals of a conventional ventilator 54. Thus, the ventilator 54 drives air through either port 48 or 50 into the respiratory system of the patient via port 46 under positive pressure and evacuates gases from the respiratory system of the patient via port 46 through the other port 50 or 48 to the ventilator 54.

Connector 26 also comprises a hollow irrigation tube 53 joined to the housing of connector 26 at hollow fitting 55. During periods of non-use, irrigation tube 53 is closed, at its distal end by a removable tethered plug 57. The irrigation tube is used to deliver an irrigation solution to the exterior of the catheter tube 22 to remove secretions therefrom during withdrawal of the catheter lube from the respiratory system of a patient and to remove secretions !rom within the catheter tube after complete withdrawal. The specific structure and exact function of the irrigation tube and related parts are set forth in U.S. Pat. No. 4,569,344, to which reference may be made. The present invention, to alleviate or overcome problems involved with prior art ventilating/aspirating apparatus, comprises a catheter tube which has an angled distal end portion 60. The angle may be on the order of 30 degrees. This facilitates predictable and easy entry of the catheter tube into either lung of a medical patient. Thus the present invention accommodates facile entry into the left lung of the distal end portion of the catheter tube in question. The distal end portion 60 of the catheter tube is illustrated in enlarged fragmentary view in FIG. 3. The distal end portion 60 in its relationship with the catheter tube 22 defines an elbow, which may comprise an included angle 62 of on the order of 150 degrees. While this particular angle is not critical, it has been found to be compatible with easy entry of the distal end portion 60 of the catheter tube 22 into the left lung of a medical patient. Apart from the curvature location 64, which may angle the distal tip of the catheter tube 22 through approximately 30 degrees, the portion of the catheter tube 22 which is proximal of the curvature site 64 is illustrated as being linear, as is the distal end portion 60 located forward of site 64.

The edge of the tip 66 of the distal end portion 60 of the catheter tube 22 is illustrated as being somewhat rounded or beveled. The catheter tube 22 including the distal end portion 60 comprises an elongated radiopaque strip 68. The radiopaque strip 68 is intentionally located so that it is within the lane which includes the curvature 64 at the inside diameter 70 thereof. While other locations can be chosen, the described location simulates the shape and identifies the exact location of the distal end portion 60. This allows the utilization of known radiological techniques during placement of the distal end portion 60 of the catheter tube 22 into a lung of a patient, particularly the left lung to insure proper positioning prior to evacuation, under negative pressure, of the secretions contained within the lung, as described above. A radiopaque band 72 may also be an aid to the radiologist, doctor, nurse or technician in properly placing the catheter tube 22 within the desired lung of a patient. Furthermore, even without use of radiological technique, the elongated radiopaque indicia allows the doctor, nurse or the like to visually orient the catheter tube for entry into the desired lung.

Figure 1:
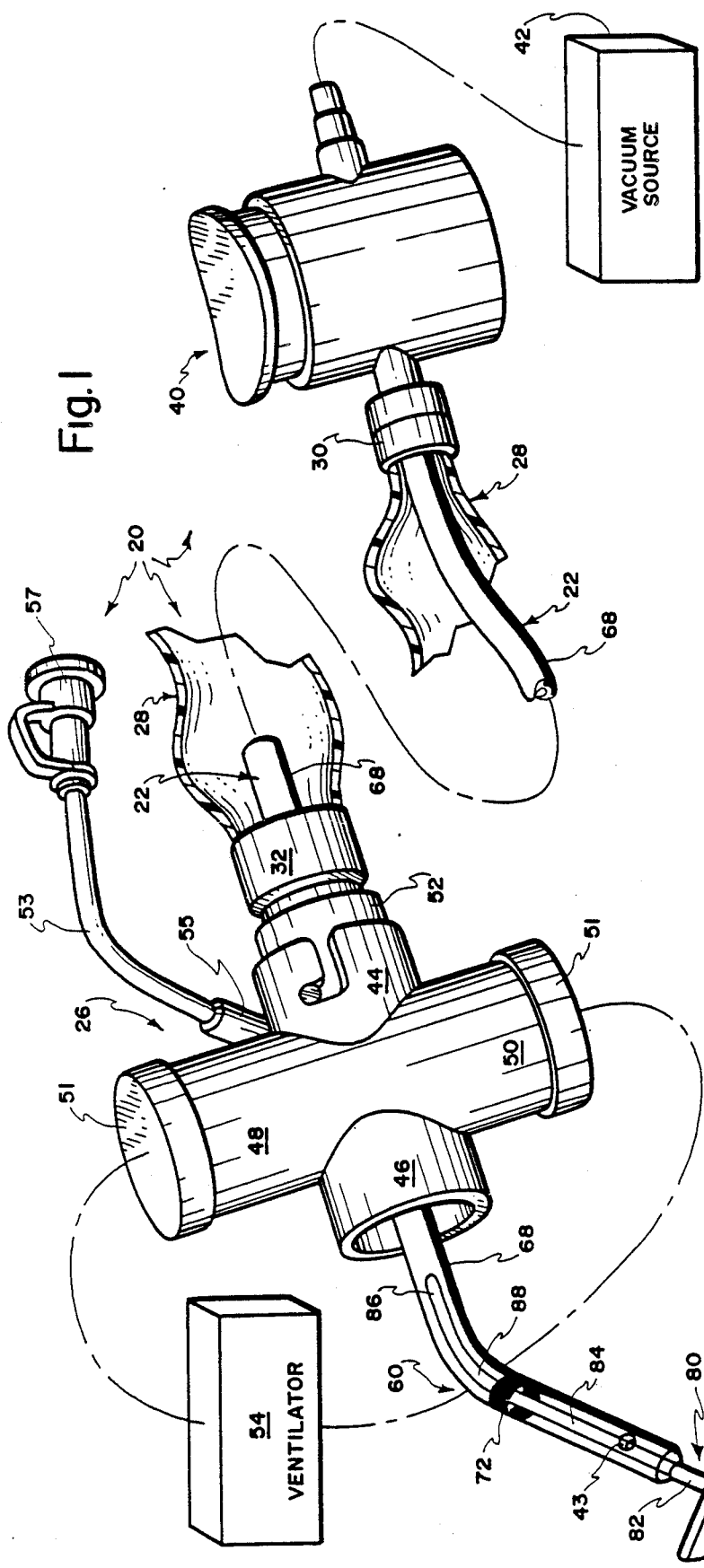
FIG. 1 is a perspective representation of a ventilating/aspirating apparatus embodying the present invention.
Figure 2:
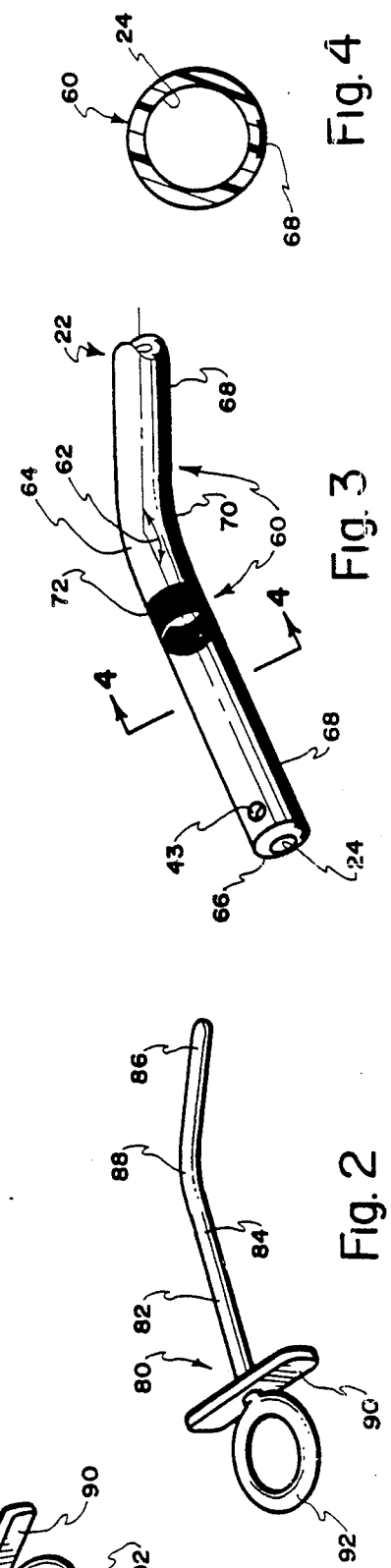
FIG. 2 is a perspective representation of the retainer by which the angle in the distal end portion of the catheter tube is retained during storage prior to use.

It is to be noted that during storage and up to the point in time when the apparatus 20 is to be used, particularly where the catheter 22 is to be used to aspirate secretions from the respiratory system of a patient, an angular retainer, generally designated 80, is removably carried primarily within the hollow interior 24 of the catheter tube 22 at the distal end portion 60. See FIG. 1. The retainer 80, as best shown in FIG. 2, comprises an elongated rod 82. Rod 82 has a straight main solid cylindrical body portion 84, which angularly connects to a straight solid cylindrical distal end portion 86. Portions 84 and 86 are connected one to another at an elbow or curvature site 88 defining an included angle equal to the angle 62. The retainer 80 is preferably comprised of a shape-retaining synthetic resinous material, such as ABS, formed using existing injection molding techniques. The proximal end of the retainer comprises an integral finger engaging cross piece 90 and a loop 92, either or both of which may be used to insert the retainer 80 into and remove it from the hollow interior 24 of the distal end portion 60 of the catheter tube 22. The outside diameter of rod 82 is substantially the same as the inside diameter at hollow 24 of the catheter tube 22 so that a snug fit is obtained. Nevertheless, the retainer 80 can be readily manually displaced into and removed from the hollow interior 24 of the catheter tube 22 at the distal end portion 60, without damage to either the catheter tube 22 or the retainer 80. Both the catheter tube 22 and the retainer 80 will flex and yield sufficiently to accommodate removal of the retainer.

Figure 3:
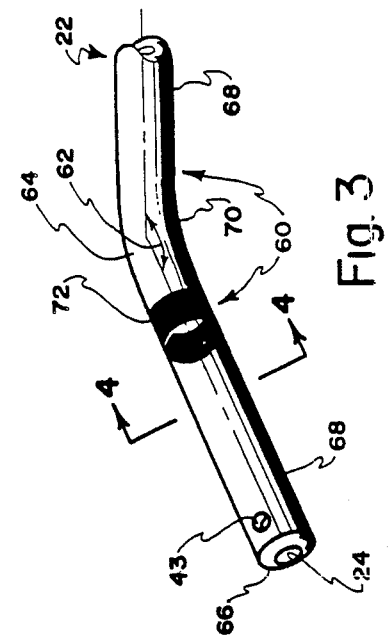
FIG. 3 is an enlarged perspective representation of the distal end portion of the catheter tube of the ventilating and aspirating apparatus of FIG. 1.

It is presently preferred that the distal end portion 60 be formed to provide the illustrated angle 62 by commencing with a catheter tube which is initially entirely linear. Thereafter, the retainer 80 is force fit into the hollow interior of the distal end of the catheter tube. This forces the distal end 60 of the catheter tube into the configuration as illustrated in FIG. 3 counter to the memory of the material comprising the catheter tube. However, if nothing more is done, the memory of the polyvinyl chloride or other synthetic resinous material from which the catheter tube 22 is made will cause the distal end 60 of the catheter tube to move from the position illustrated in FIG. 3 toward an entirely linear configuration once the retainer 80 is removed.

To the contrary, with the retainer 80 in place, the distal end portion 60 of the catheter tube 22 is subjected to heat. Preferably a stream of hot air, until memory forces within the material from which the catheter tube is made are negated at the tip thereof and the angle 62 becomes substantially permanent, subject to the inherent yieldable nature of the material. Accordingly, under non-stress conditions the distal end portion 60 of the catheter tube 22 will tend to remain disposed at angle 62. It has been found that a stream of hot air having a temperature of about 110 degrees celcius applied over an interval of time of 10 seconds to the distal end portion 60 of polyvinyl chloride catheter tube 22 will produce he required memory relief and new set in the material at the distal end portion 60 sufficient to retain the angle 62 under non-stress conditions when the retainer 80 is removed.

The invention may be embodied in other specific forms without departing from the spirit or essential characteristics thereof. The present embodiment is, therefore, to be considered in all respects as illustrative and not restrictive, the scope of the invention being indicated by the appended claims rather than by the foregoing description, and all changes which come within the meaning and range of equivalency of the claims are therefore to be embraced therein.

What is claimed and desired to be secured by United States Letters Patent is:

1. An indwelling apparatus by which a medical patient is subject to involuntary respiratory therapy and by which secretions in the trachea and/or bronchi are evacuated, the apparatus during storage and prior to use comprising:

an elongated aspirating catheter tube comprising a main portion comprising a longitudinal axis having a hollow interior axial passageway and comprising relatively small inside and outside diameters, an essentially free distal end portion for manual insertion into the lungs of a patient and axially disposed suction port means disposed at the distal tip of the catheter tube in fluid communication with the axial passageway;

the free distal end portion of the catheter tube immediately proximal of the suction port means being shaped so that at the time of inception of the apparatus it bears a sharp acute angular relationship to the longitudinal axis whereby facile accurate entry into the left lung of the patient is predictably accommodated;

retainer means comprising a shaft defining a fixed predetermined angle substantially the same as the sharp acute angle formed by the distal end portion of the catheter tube removably coextensively disposed in the distal end of the axial passageway at the time of inception of the apparatus, the retainer means projecting distally beyond the suction port means for retaining said sharp acute angle in the distal end of the catheter tube after inception and during storage of the apparatus whereby shaping of the distal end portion of the catheter tube immediately prior to use in obviated, the retainer means further comprising handle means exposed beyond the distal tip of the catheter tube by which the fixed angle shaft of the retainer means is inserted and removed.

2. An indwelling apparatus according to claim 1 wherein the distal end portion of the catheter tube is essentially straight, the straight distal end portion joining the remainder of the catheter tube at an elbow comprising said predetermined sharp angle, when in an unstressed condition.

3. An indwelling apparatus according to claim 2 wherein the sharp angle is on the order of 30 degrees in respect to the remainder of the catheter tube, when in an unstressed condition.

4. A method of making and storing an aspirating apparatus comprising the steps of:

creating a linear elongated aspirating catheter tube formed as one piece from a suitable synthetic resinous material having a hollow interior, an essentially free distal end portion for insertion into the respiratory system of a medical patient under the manual control of a user and axially-oriented distal tip suction port means in communication with the hollow interior;

at inception of the apparatus, providing a long term shape-retaining retainer comprising rod means having two substantially linear sections integrally joined by an elbow comprising a predetermined sharp fixed acute included angle;

at inception of the apparatus and before packaging, assembling the catheter tube and the retainer by inserting the fixed angle rod means of the retainer through the axially-oriented distal suction port means and a predetermined distance into the distal region of the hollow interior of the aspirating catheter tube thereby causing only the distal end portion of the aspirating catheter tube to conform to the sharp angular configuration of the rod means counter to the memory forces of the material from which the aspirating catheter tube is formed;

at inception of the apparatus and before packaging, subjecting the distal end portion of aspirating catheter tube to heat of a temperature and for a time sufficient to permanently substantially negate said memory forces;

storing the assembled heat treated catheter tube and the long term retainer in the angular assembled condition after inception and during a period of storage up to the time insertion of the aspirating catheter tube into the respiratory system of the medical patient is imminent whereby shaping of the distal region of the catheter tube immediately prior to use is obviated;

removing the rod means from the hollow interior of the aspirating catheter tube at the distal end portion thereof via the suction port means immediately prior to insertion of the aspirating catheter tube into said respiratory system while performing no work on the distal end region of the aspirating catheter tube, the distal end region, upon withdrawal of the rod means from the hollow thereof, tending to remain in the sharp angular configuration corresponding to the fixed angular configuration of the rod means in the absence of stress imposed thereon to the contrary.

* * * * *

UNITED STATES PATENT AND TRADEMARK OFFICE
CERTIFICATE OF CORRECTION

PATENT NO. : 4,981,466

DATED : January 1, 1991

INVENTOR(S) : Richard C. Lambert

It is certified that error appears in the above-identified patent and that said Letters Patent is hereby corrected as shown below:

Title page, left-hand column, Item [19] and [76]:
change "Lumbert" to --Lambert--.

Signed and Sealed this

Seventh Day of July, 1992

Attest:

DOUGLAS B. COMER

*Attesting Officer*   Acting Commissioner of Patents and Trademarks